(12) United States Patent
Zhu et al.

(10) Patent No.: US 7,037,273 B2
(45) Date of Patent: May 2, 2006

(54) CORE BODY TEMPERATURE MONITORING IN HEART FAILURE PATIENTS

(75) Inventors: Qingsheng Zhu, Little Canada, MN (US); Julio Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 528 days.

(21) Appl. No.: 10/154,142

(22) Filed: May 22, 2002

(65) Prior Publication Data

US 2003/0220582 A1   Nov. 27, 2003

(51) Int. Cl.
*A61B 5/00* (2006.01)
(52) U.S. Cl. .................... 600/549; 600/482; 607/21
(58) Field of Classification Search ........... 607/17–23; 600/549, 482, 483
See application file for complete search history.

(56) References Cited

U.S. PATENT DOCUMENTS

| | | | | |
|---|---|---|---|---|
| 5,029,582 | A * | 7/1991 | Lekholm ................... | 607/21 |
| 5,044,366 | A * | 9/1991 | Alt ............................ | 607/18 |
| 5,336,244 | A * | 8/1994 | Weijand .................... | 607/21 |
| 5,454,838 | A * | 10/1995 | Vallana et al. ............ | 607/19 |
| 6,249,700 | B1 * | 6/2001 | Alt ............................ | 607/4 |
| 6,662,048 | B1 * | 12/2003 | Balczewski et al. ...... | 607/21 |
| 2003/0125774 | A1 * | 7/2003 | Salo .......................... | 607/21 |
| 2003/0167081 | A1 * | 9/2003 | Zhu et al. ................. | 607/122 |

OTHER PUBLICATIONS

Stanley A. Rubin, Core Temperature Regulation of Heart Rate During Exercise In Humans, *Division of Cardiology, Cedars-Sinai Medical Center, and Department of Medicine, University of California, Los Angeles, California*, 1987, p. 1997-2002.

Frank G. Shellock, H.J.C. Swan, and Stanley A. Rubin, "Muscle and Femoral Vein Temperatures During Short-Term Maximal Exercise in Heart Failure," *Division of Cardiology, Cedars-Sinai Medical Center, and Department of Medicine, University of California, Los Angeles, California*, Feb., 1985, p. 400-408.

(Continued)

*Primary Examiner*—Robert Nasser
(74) *Attorney, Agent, or Firm*—Merchant & Gould (57) ABSTRACT

An implanted heart monitor includes sensors that measure various aspects of the heart failure patient's heart. A remote heart monitoring system connects the implanted heart monitor to a care provider, such as a physician. The data provided by the implanted heart monitor permits the care provider to obtain valuable data on the heart in order to make health care decisions affecting the heart failure patient's treatment. In many cases, the measurement of core body temperature and other patient data will enable the care provider to alter the patient's treatment to address the patient's condition. The implanted heart monitor can communicate over a wireless communication link with an external monitor. The implanted heart monitor may be implemented as part of a pacing device (i.e., pace maker) or may be a separate unit devoted to monitoring functions. The external monitor communicates with a monitoring station over a communication link. The monitoring station can operate as a centralized data collection unit, collecting data from multiple external monitors and multiple implanted heart monitors. Various other aspects of a heart failure patient's heart and/or body can be monitored, such as heart rate, blood pH levels, blood $CO_2$ levels, and any other indications of the heart failure patient's activity. Various predetermined thresholds may be set to trigger alarms and/or data reports.

31 Claims, 4 Drawing Sheets

OTHER PUBLICATIONS

Frank G. Shellock and Stanley A. Rubin, "Mixed Venous Blood Temperature Response To Exercise in Heart Failure Patients Treated With Short-Term Vasodilators," *Division of Cardiology, Cedars-Sinai Medical Center, and Department of Medicine, University of California, Los Angeles, California*, Dec., 1985, p. 503-514.

Neal E. Fearnot, Heidi J. Smith, Dunan Sellers, Duncan and Bernard Boal, "Evaluation of the Temperature Response to Exercise Testing in Patients With Single Chamber, Rate Adaptive Pacemakers: A Multicenter Study," *Pacing and Clinical Electrophysiology (US)*, vol. 12, Nov., 1989, p. 1806-1815.

Patricia A. McElroy, Joseph S. Janicki, Karl T. Weber, "Physiolotic Correlates of the Heart Rate Response to Upright Isonotic Exercise: Relevance to Rate-Responsive Pacemakers," *Journal of the American College of Cardiology (US)*, vol. 11, No. 1, Jan., 1988, p. 94-99.

S. Walker, T.M. Levy, A.J.S. Coats, N.S. Peters and V.E. Paul on Behalf of the Imperial College Cardiac Electrophysiology Group, Imperial College, Lond, U.K., "Bi-Ventricular Pacing In Congestive Cardiac Failure, Current Experience and Future Directions," *European Heart Journal (England)*, vol. 21, No. 11, Jun., 2000, p. 884-889.

D. Farwell, N.R. Patela, A. Hall, S. Ralph and A. N. Sulke, "How Many People With Heart Failure Are Appropriate for Biventricular Resynchronization?", *European Heart Journal (England)*, vol. 21, No. 15, Aug., 2000, p. 1246-1250.

C. Alonso, C. Leclercq, F. Victor, H. Mansour, C. de Place, D. Pavein, F. Carré, P. Mabo, and J. C. Daubert, "Electrocardiographic Predictive Factors of Long-Term Clinical Improvement With Multisite Biventricular Pacing In Advanced Heart Failure," *The American Journal of Cardiology (US)y*, vol. 84, No. 12, Dec. 1999, p. 1417-1421.

P. le Franc, D. Klug, D. Lacroix, M. Jarwe, C. Kouakam, and S. Kacet, "Triple Chamber Pacemaker for End-Stage Heart Failure in a Patient With a Previously Implanted Automatic Defibrillator," *Pacing and Clinical Electrophysiology (US)*, vol. 21, No. 8, Aug. 1998, p. 1672-1675.

\* cited by examiner

CORE BODY TEMPERATURE MONITORING IN HEART FAILURE PATIENTS

FIELD OF THE INVENTION

The present invention relates to monitoring heart performance in heart failure patients. More specifically, the present invention relates to monitoring heart performance to detect the occurrence of a drop in core body temperature in heart failure patients.

BACKGROUND OF THE INVENTION

As early as 1985, medical literature documented a relationship between decreased core body temperature and increased bodily activity in heart failure patients. In a paper by Stanley A. Rubin (RUBIN, STANLEY A. *Core body temperature regulation of heart rate during exercise in humans.* J. Appl. Physiol. 62(5): 1997–2001, 1987), a significant correlation was found between an observed change in core body temperature and heart rate changes in heart failure patients. Rubin defined core body temperature as the mixed venous blood pool found in the pulmonary artery. Using a thermistor mounted on the distal end of a Swan-Ganz catheter, Rubin found that the core body temperature of heart failure patients decreased during exercise, while the core body temperature in normal patients typically increased during exercise.

This relationship between core body temperature and heart activity has been observed in other studies. In a paper by Frank G. Shellock, et al. (SHELLOCK, FRANK G., H. J. C. SWAN, AND STANLEY A. RUBIN. *Muscle and femoral vein temperatures during short term maximal exercise in heart failure.* J. Appl. Physiol. 58(2): 400–408, 1985), reductions in core body temperatures in heart failure patients were observed while the heart failure patients underwent exercise. Shellock, et al. concluded that the core body temperature decrease observed in heart failure patients is partially caused by the re-distribution of cooler blood from the underperfused skeletal muscles into the core blood during exercise. Another paper by Shellock and Rubin (FRANK G. SHELLOCK AND STANLEY A. RUBIN. *Mixed venous blood temperature response to exercise in heart failure patients treated with short-term vasodilators.* Clinical Physiology 5, 503–514, 1985), also concluded that the core body temperature drop was due to circulatory inadequacies. This conclusion was based on Shellock's and Rubin's conclusion that heart failure patients treated with vasodialators experience an attenuation of the core body temperature response typical during exercise, as a result of vasodialator-induced improvement in circulation.

More recent research ascribes the drop in core body temperature to low blood pH levels. As a heart failure patient exercises, the heart failure patient experiences an increase of $CO_2$ in its blood as the blood attempts to eliminate the $CO_2$ from the exercising muscles. The heart failure patient will normally increase its breathing volume in an attempt to evacuate the increased level of $CO_2$ from the blood. However, in heart failure patients, the blood system cannot deliver the blood to the lungs fast enough to support an adequate $CO_2$ for $O_2$ exchange in the lungs. It is well known that higher levels of $CO_2$ correlate with lower levels of blood pH. As $CO_2$ accumulates in the heart failure patient's body, the blood's pH level drops. Because pH is a catalyst for virtually every chemical reaction in the body, the heart failure patient's chemical reactions will be slowed by the reduced pH levels. As the blood's pH level drops with the increased $CO_2$ levels, the heart failure patient's bodily chemical reactions responsible for heat production during exercise are slowed and the core body temperature stays flat or decreases.

While the core body temperature drop phenomenon has been documented in the literature described above, little has been done to apply this knowledge to benefit heart failure patients. A heart failure patient may require immediate medical attention or an alteration of medical treatment in certain conditions where an increase in heart activity and a decrease in core body temperature are coincident.

Therefore, there is a need in the art for a core body temperature monitoring system that can determine when the core body temperature level of a heart failure patient is outside of an acceptable range. The monitoring system also should determine whether the relationship between the core body temperature level and the activity of the heart failure patient is outside of an acceptable range. The monitoring system should be capable of generating an alarm when an unacceptable level has been detected. The monitoring system also should be able to transmit an alarm to a remote location.

SUMMARY OF THE INVENTION

An implanted heart monitor of the present invention includes sensors that measure various aspects of the heart failure patient's heart. A remote heart monitoring system can connect the implanted heart monitor to a care provider, such as a physician. The data provided by the implanted heart monitor permits the care provider to obtain valuable data on the heart in order to make health care decisions affecting the heart failure patient's treatment. In many cases, the measurement of core body temperature and other patient data will enable the care provider to alter the patient's treatment to address the patient's condition. The implanted heart monitor can communicate over a wireless communication link with an external monitor. The implanted heart monitor may be implemented as part of a pacing device (i.e., pace maker) or may be a separate unit devoted to monitoring functions. The external monitor communicates with a monitoring station over a communication link. The monitoring station can operate as a centralized data collection unit, collecting data from multiple external monitors and multiple implanted heart monitors. Various other aspects of a heart failure patient's heart and/or body can be monitored, such as heart rate, blood pH levels, blood $CO_2$ levels, and any other indications of the heart failure patient's activity. Various predetermined thresholds may be set to trigger alarms and/or data reports.

In one aspect of the present invention, a heart monitoring system is provided. The heart monitoring system includes a temperature sensor for determining a core body temperature of a patient and a bodily activity sensor for determining a bodily activity level of the patient. A communication link is used for transmitting the core body temperature and the bodily activity level to an external monitor.

In another aspect of the invention, a method is provided for diagnosing a performance level of a heart in a patient. A core body temperature and a bodily activity level are determined. A relationship between the core body temperature and the bodily activity level is also determined. In response to determining that the relationship between the core body temperature and the bodily activity level is outside of a predetermined acceptable relationship range, a first alarm message is generated.

In yet another aspect of the invention, an implantable heart monitor is provided. The implantable heart monitor has a core body temperature sensor for determining a core body temperature of a patient. A bodily activity sensor is used to determine a bodily activity level of a patient. The implantable heart monitor also has a transmission unit for transmitting the core body temperature and the bodily activity level to an external monitor and a processing unit for calculating a relationship between the core body temperature and the bodily activity level and for generating an alarm message in response to a determination that the relationship is outside of a predefined acceptable range. The transmission unit can transmit the alarm message to the external monitor.

The various aspects of the present invention may be more clearly understood and appreciated from a review of the following detailed description of the disclosed embodiments and by reference to the drawings and claims.

DETAILED DESCRIPTION

In an exemplary embodiment of the present invention, an implanted heart monitor includes sensors that measure various aspects of a heart failure patient's heart. A remote heart monitoring system connects the implanted heart monitor to a care provider, such as a physician. The data provided by the implanted heart monitor permits the care provider to obtain valuable data on the heart in order to make health care decisions affecting the heart failure patient's treatment. In many cases, the measurement of core body temperature and other patient data will enable the care provider to alter the patient's treatment to address the patient's condition. The implanted heart monitor can communicate over a wireless communication link with an external monitor. The implanted heart monitor may be implemented as part of a pacing device (i.e., pace maker) or may be a separate unit devoted to monitoring functions. The external monitor communicates with a monitoring station over a communication link. The monitoring station can operate as a centralized data collection unit, collecting data from multiple external monitors and multiple implanted heart monitors. Various other aspects of a heart failure patient's heart and/or body can be monitored, such as heart rate, blood pH levels, blood $CO_2$ levels, and any other indications of the heart failure patient's activity. Various predetermined thresholds may be set to trigger alarms and/or data reports.

Figure 1:
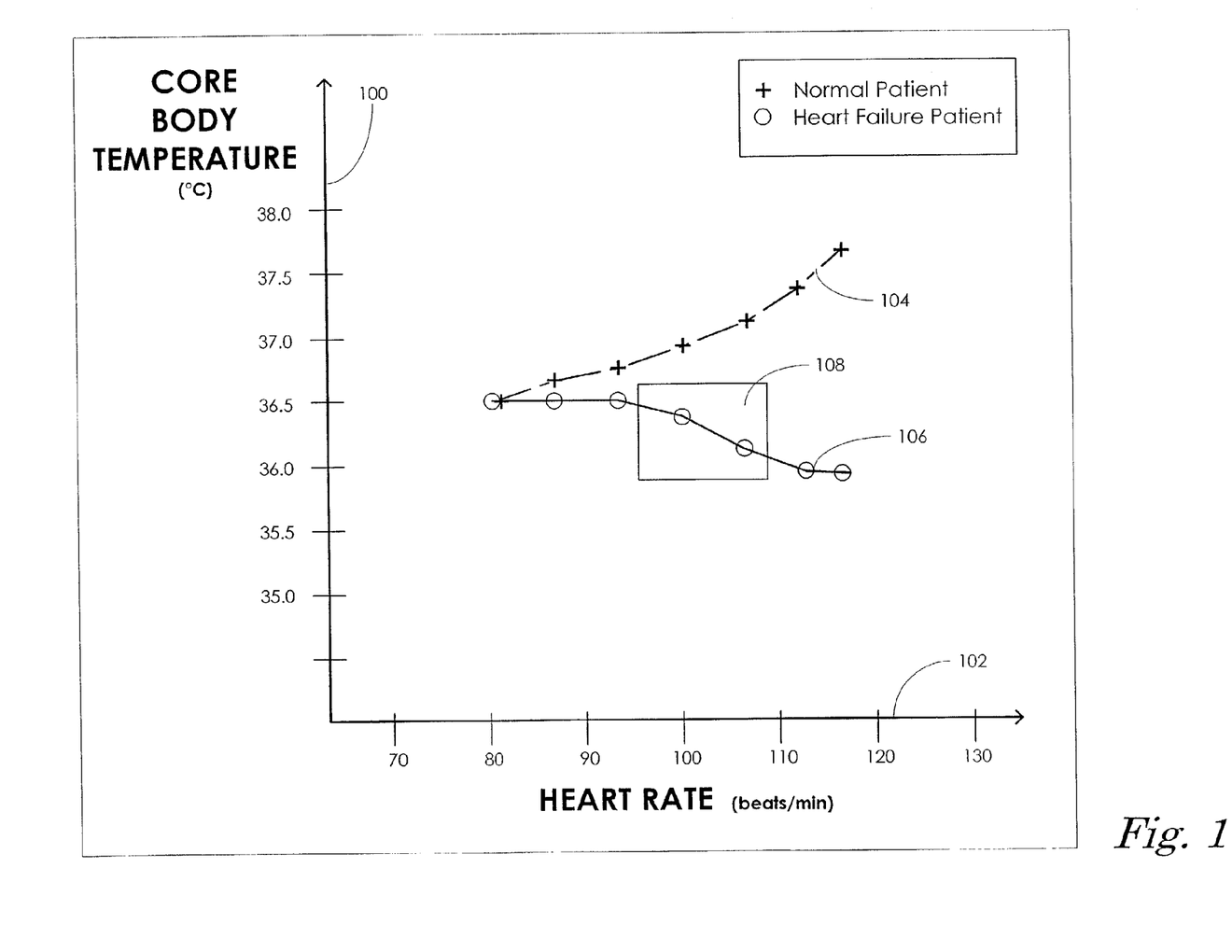
FIG. 1 is a graph depicting an exemplary relationship between observed core body temperature measurements and heart rate measurements in normal patients and in heart failure patients.

FIG. 1 is a graph depicting an exemplary relationship between observed core body temperature measurements and heart rate measurements in normal patients and in heart failure patients. The graph of FIG. 1 is a two-dimensional graph with core body temperature levels indicated on the y axis 100 in degrees Celsius and heart rate levels indicated on the x axis 102 in beats per minute. The graph of FIG. 1 relates core body temperature measurements and heart rate temperature measurements for normal patients along normal curve 104. The graph of FIG. 1 relates core body temperature measurements and heart rate measurements for heart failure patients along the heart failure patient curve 106.

As can be seen from the graph, in normal patients, core body temperature increases in approximately a direct relationship with an increase in heart rate. In heart failure patients, on the other hand, core body temperature stays constant or is reduced as the heart failure patient's heart rate increases. As described above, this phenomenon has been well documented in medical literature. As mentioned above, recent research ascribes the drop in core body temperature to low blood pH levels. As a heart failure patient exercises, the heart failure patient experiences an increase of $CO_2$ in its blood as the blood attempts to eliminate the $CO_2$ from the exercising muscles. The heart failure patient will normally increase its breathing volume in an attempt to evacuate the increased level of $CO_2$ from the blood. However, in heart failure patients, the blood system cannot deliver the blood to the lungs fast enough to support an adequate $CO_2$ for $O_2$ exchange in the lungs. It is well known that higher levels of $CO_2$ correlate with lower levels of blood pH. As $CO_2$ accumulates in the heart failure patient's body, the blood's pH level drops. Because pH is a catalyst for virtually every chemical reaction in the body, the heart failure patient's chemical reactions will be slowed by the reduced pH levels. As the blood's pH level drops with the increased $CO_2$ levels, the heart failure patient's bodily chemical reactions responsible for heat production during exercise are slowed and the core body temperature stays flat or decreases, In the graph of FIG. 1, a critical zone 108 has been defined. Although the critical zone 108 could be tailored for any diagnostic and/or treatment purposes, it represents the occurrence of a critical event in the relationship between the core body temperature and the heart rate. In the case of FIG. 1, the negative slope of heart failure patient curve 106 indicates that the core body temperature is dropping rapidly as the patient's heart rate increases. By monitoring the slope of the heart failure patient curve 106, a care provider (e.g., attending physician) could determine that a heart failure patient is experiencing adverse heart conditions. In response to this determination, the care provider could alter the patient's medical treatment or instruct the patient to seek medical attention. In the example of FIG. 1, heart rate is used as an indicator of a heart failure patient's bodily activity. Typically, increased bodily activity results in increased heart rate. However, as is well known in the art, a heart failure patient's heart rate can increase for various reasons. Thus, monitoring heart rate alone is not necessarily an indication that the heart failure patient is experiencing increased bodily activity. Those skilled in the art will also appreciate that other aspects of the heart failure patient's diagnostics can be used to indicate increased bodily activity. Such data may include breathing volume, patient motion, and $CO_2$ levels.

Core body temperature is indicative of the temperature of blood returning to the heart from the rest of patient's body. Of course, core body temperature can increase and decrease for various reasons. Consequently, the increase or decrease in core body temperature alone is not necessarily indicative of an adverse heart condition. A concurrent decrease in core body temperature and increase in patient bodily activity is indicative of an adverse heart condition. Consequently, exemplary embodiments of the present invention enable more effective treatment of a heart failure patient by monitoring the relationship between core body temperature and heart rate (or other indications of bodily activity).

Figure 2:
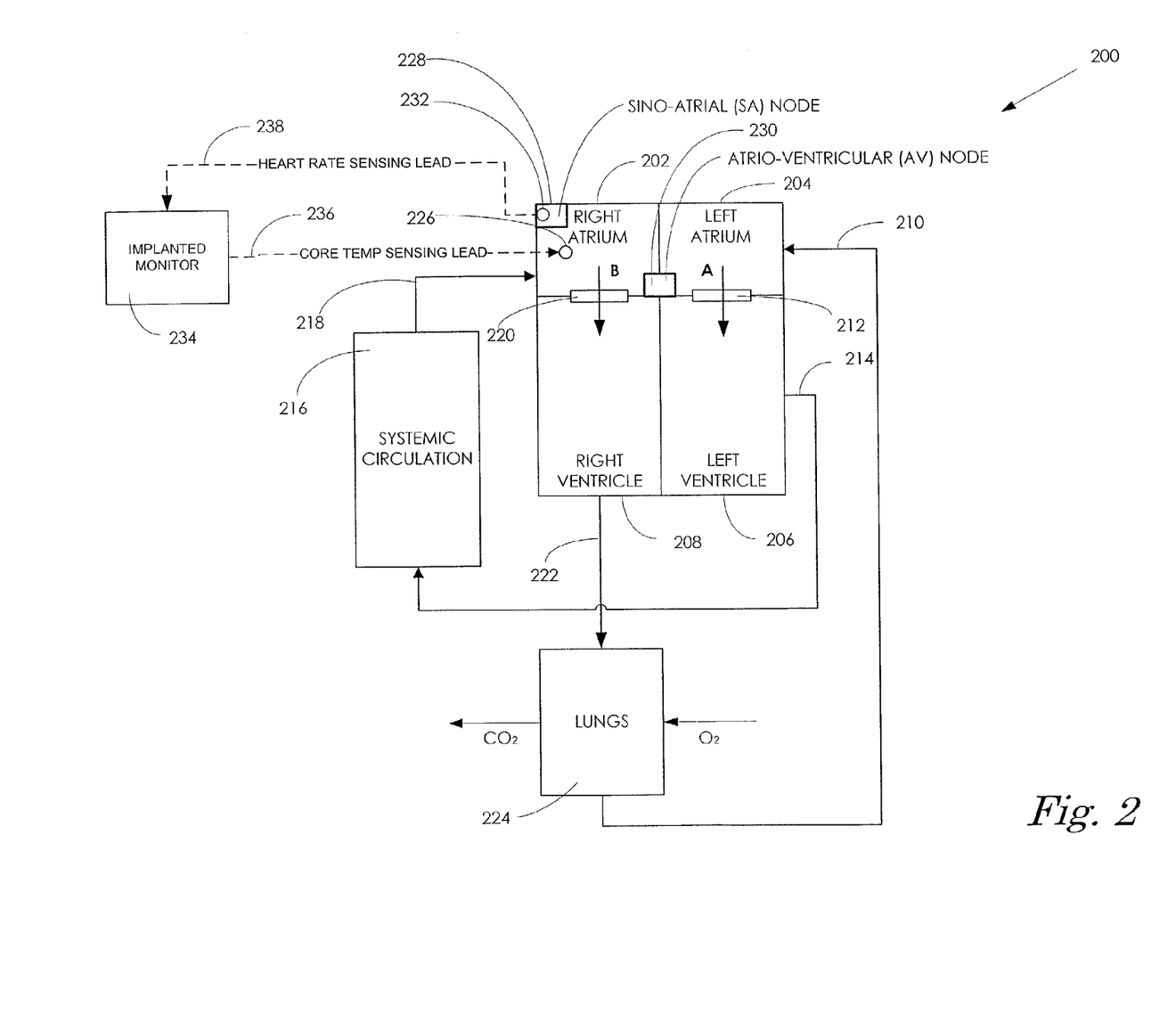
FIG. 2 is a block diagram depicting the blood system of a heart failure patient with an implanted heart monitor that is an exemplary embodiment of the present invention.

FIG. 2 is a block diagram depicting the blood system of a heart failure patient with a heart monitor that is an exemplary embodiment of the present invention. The typical heart 200 includes a right atrium 202, a left atrium 204, a right ventricle 208, and a left ventricle 206. The left atrium 204 brings in arterialized blood from the lungs through the pulmonary veins 210. The pumping action of the heart 200 forces blood from the left atrium 204 to the left ventricle 206 through a one-way left heart valve 212 in the direction of arrow A. The pumping action of the heart 200 forces blood from the left ventricle 206 through the aorta 214 to the body's systemic circulation system 216. The systemic circulation system 216 is a short-hand reference to the network of blood vessels that distribute blood to all parts of the body. Blood is returned to the heart 200 from the systemic circulation system 216 through the venae cavae 218. The returning blood is characterized by having a higher $CO_2$ content. The blood transports oxygen to the systemic circulation system 216 and eliminates $CO_2$ from the systemic circulation system.

Blood with high $CO_2$ content enters the right atrium 202 through the venae cavae 218. The pumping action of the heart forces blood from the right atrium 202 to the right ventricle 208 through a one-way right heart valve 220 in the direction of arrow B. The pumping action of the heart then forces the blood from the right ventricle 208 through the pulmonary artery 222 to the lungs 224. The blood is ultimately forced into capillaries in the lungs that expose the blood to air sacs. The air sacs of the lung 224 provide the architecture for exchanging $CO_2$ in the blood for oxygen in the lungs. Once the exchange has been made, the blood is forced from the lungs back into the heart 200 through the pulmonary veins 210.

Core body temperature is normally measured in the return path of the blood circulation system. Because all of the body's blood returns through the venae cavae 218 to the right atrium 202, the blood entering the right atrium is referred to as the mixed venous blood pool. Notably, the blood in the venous blood pool has dissipated as much heat as possible in the systemic circulation system 216 prior to re-entering the heart 200. A temperature sensor, such as a thermistor, can be placed in or near the right atrium 202 to measure the core body temperature in the venous blood pool. In a one embodiment as shown in FIG. 2, a core body temperature sensor 226 is located inside the right atrium 202. Those skilled in the art will appreciate the core body temperature may be measured in various locations in addition to a location in the right atrium 202. For example, measurements of skeletal muscle temperature, myocardial muscle temperature, or even skin temperature can be measured and correlated to a corresponding core body temperature to determine the measured core body temperature. In a practical application, a core body temperature sensor could be integrated into the outer casing of a conventional implanted pacing device. A temperature correlation table could be used to approximate the core body temperature, based on the temperature detected at the pacing device casing.

The right atrium 202 includes a sino-atrial (SA) node 228. The SA node 228 signals an electrical impulse to propagate through the heart 200 to cause the heart to beat. The SA node receives an electrical impulse from the nervous system and converts the electrical impulse to a heartbeat. An atrio-ventricular (AV) node 230 is a cluster of muscle cells located in the wall between the right atrium 202 and the left atrium 204. The AV node 230 is part of the heart's 200 electrical system. The AV node 230 helps deliver heartbeat signals from the atria to the ventricles. Heart rate measurements are often taken at the SA node 228, because the SA node is the contact point from which the body's natural heart pacing signals emanate. Even in heart failure patients, the SA node 228 will usually receive a detectable signal from the nervous system. The natural heart-pacing signal can be detected by means of a heart rate sensing lead 232, attached to the heart 200 at the SA node 228.

The core body temperature sensor 226 and the heart rate sensor 232 can be connected to an implanted monitor 234 by a core body temperature sensing lead 236 and a heart rate sensing lead 238, respectively. The implanted monitor 234 can be an integrated component of a pacing device or may simply be an implanted monitor with no pacing functionality. In an exemplary embodiment of the present invention, the implanted monitor 234 can communicate with an external monitor (not shown) to communicate various data collected from the patient and/or analysis performed on collected data. In any event, the implanted monitor 234 can measure heart rate and core body temperature data and can transmit that data to an external entity such as a care provider, an external monitor/alarm unit, or an external data collection center.

The implanted monitor 234 also can determine the relationship between collected data such as core body temperature and heart rate data. For example, the implanted monitor 234 could be used to calculate the slope of a graph of the relationship between a heart failure patient's heart rate and core body temperature measurements. As described above, the data collected and/or analyzed by the implanted monitor 234 may include various indications of bodily activity and/or heart performance.

Figure 3:
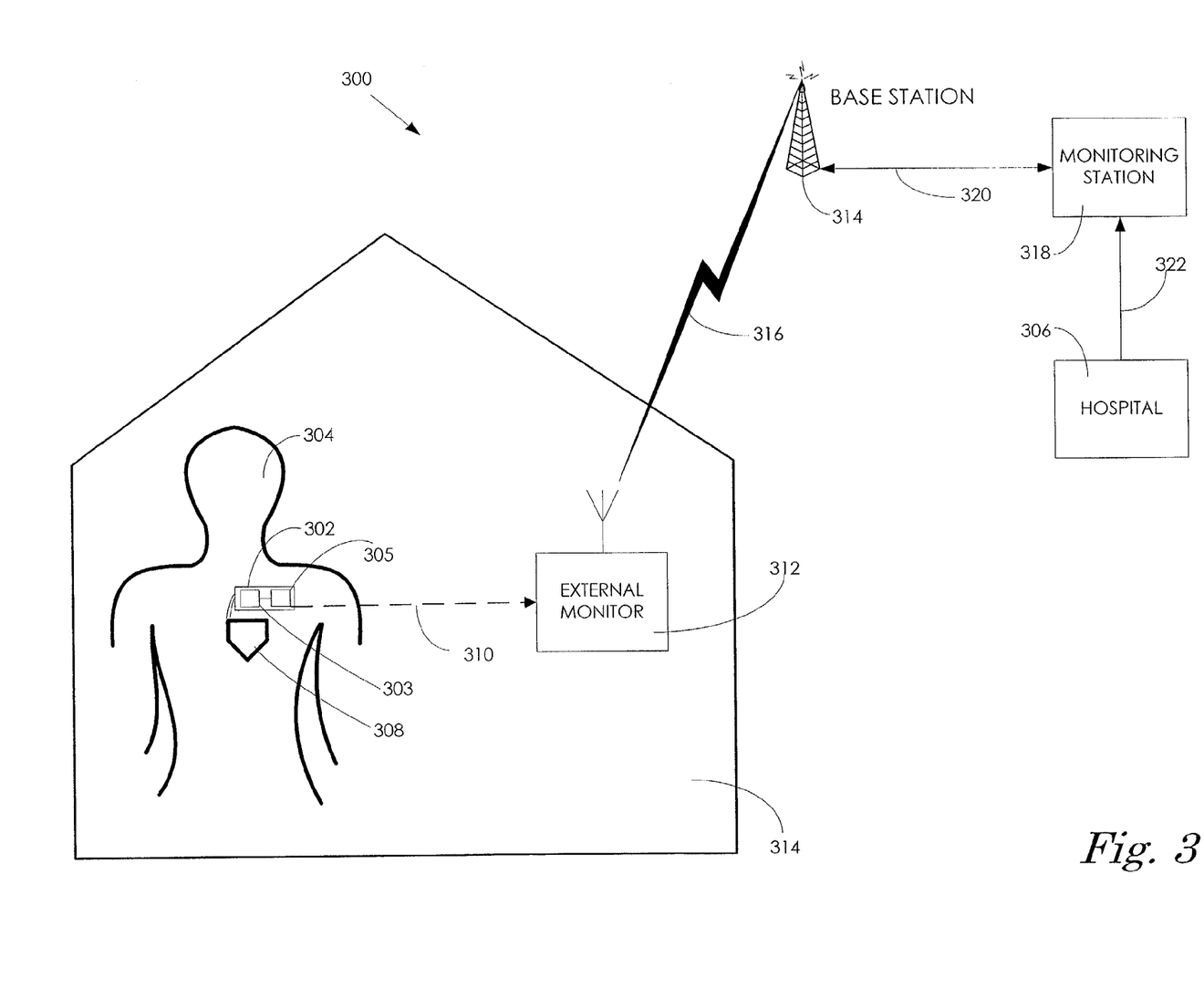
FIG. 3 is a block diagram of a remote heart monitoring system that is an exemplary embodiment of the present invention.

FIG. 3 is a block diagram of a remote heart monitoring system 300 that is an exemplary embodiment of the present invention. The remote heart monitoring system 300 connects a heart monitor 302, implanted in a heart failure patient 304, to a care provider (e.g., a physician), for example, a physician at a hospital 306. The implanted heart monitor 302 includes sensors that measure various aspects of the heart failure patient's heart 308. The implanted heart monitor 302 can include a processing unit 303 for processing the measured data and for analyzing the data to, for example, determine a relationship between the measured data. The implanted heart monitor 302 communicates over a wireless communication link 310 with an external monitor 312. The implanted heart monitor 302 may include a transmission unit 305 for communicating with the external monitor over the wireless communication link 310.

The implanted heart monitor 302 may be implemented as part of a pacing device (i.e., pace maker) or may be a separate unit devoted to monitoring bodily functions. The external monitor can be located within the heart failure patient's home 314 or may be mobile. Those skilled in the art will appreciate that various implementations of the external monitor 312 are possible within the scope of the present invention. It should also be appreciated that the connection between the implanted heart monitor 302 and the external monitor 312 could be a hardwire connection (i.e., not wireless), for example, when the remote heart monitoring system 300 is used in a hospital room context.

The external monitor 312 communicates with a base station 314 over a wireless communication link 316. Again, those of ordinary skilled in the art will appreciate that a hardwire connection could be used between the external monitor 312 and the base station 314. However, as with the wireless communication link 310 between the implanted heart monitor 302 and the external monitor 312, the wireless communication link 316 provides the most versatility and convenience to the patient.

The base station 314 is connected to a monitoring station 318 over a communication link 320. The monitoring station can be used to collect data from the implanted heart monitor 302, via the external monitor 312. Notably, the monitoring station 318 can collect data from multiple external monitors and multiple implanted heart monitors. That is, the monitoring station 318 can operate as a centralized data collection unit. The monitoring station 318 can communicate with a hospital 306 over a communication link 322. The monitoring station 318 can communicate with multiple hospitals and/or care providers to deliver monitored and/or stored data.

In the remote heart monitoring system 300 of FIG. 3, various aspects of a heart failure patient's heart and/or body can be monitored. For example, the implanted heart monitor 302 may monitor core body temperature, ventilation rate, oxygen consumption rate, heart rate, blood pH levels, blood $CO_2$ levels, bodily movement, and any other indication of the heart failure patient's bodily activity. Various predetermined thresholds may be set to trigger alarms and/or data reports. For example, if the heart monitor 302 determines that the measured core body temperature is outside a predefined acceptable range, the heart monitor may trigger an alarm. Alternatively, the heart monitor 302 may simply deliver the data to the external monitor 312.

The external monitor 312 may compare the measured levels to predetermined acceptable ranges and trigger alarms when a variance is detected. Similarly, predetermined thresholds may be set for the heart failure patient's heart rate and for the relationship between measured indications. For example, an alarm may be triggered when the slope of a graph of core body temperature versus heart rate is too low.

While the remote heart monitoring system 300 of FIG. 3 has been described in the context of monitoring the conditions of a heart failure patient, it will be appreciated by those skilled in the art that the remote monitoring system could be implemented to monitor virtually any aspect of a patient's health or activity.

The implanted heart monitor 302 periodically collects data and reports the collected data to the external monitor 312. The external monitor 312 can process the data and relay the data to the monitoring station 318 at predetermined intervals, via the base station 314. The external monitor 312 may make a determination that the collected data indicates a change in patient wellness. In response to a determination that the patient's wellness has improved or declined, the external monitor 312 may generate a wellness report separate from the routinized collected data reporting. The external monitor 312 may determine that the collected data justifies the transmission of an alarm. In this case, the external monitor 312 can transmit an alarm request to the monitoring station that can then generate an alarm and convey the alarm to the appropriate care provider at the hospital 306. Those skilled in the art will appreciate that the functionality of the implanted monitor and of the external monitor could be integrated into a single unit. It will also be appreciated that the implanted monitor could detect and transmit virtually any heart condition and/or body condition data.

The heart monitoring system 300 of FIG. 3 could be used in conjunction with a pacing device or any other heart failure treatment regimen. When the implanted heart monitor 302 detects an out-of-range condition, an alarm may be generated for the care provider, as described above. If, for example, the core body temperature measurement is outside of a predefined acceptable range, the care provider may access the patient's historical records to determine potential causes. The care provider also may cause the monitoring station 318 to initiate special communications with the external monitor 312 to gather more recent data on the patient's heart or other diagnostic information. If the care provider receives an alarm indicating a relationship between the core body temperature and the bodily activity level, the care provider may contact the patient and urge the patient to seek immediate treatment. Of course, in a hospital context, the care provider may simply go to the patient's hospital room and attend to the patient.

Generally, a significant decrease in a heart failure patient's core body temperature without a coincident increase in bodily activity may signal an imminent heart failure episode, such as cardiac arrest. A decrease in a heart failure patient's core body temperature that is coincident with an increase in bodily activity is an expected relationship. However, if the decrease in core body temperature during increased bodily activity is too rapid, it too may signal an imminent heart failure episode, such as cardiac arrest. In any event, the data provided by the implanted heart monitor permits the care provider to obtain valuable data on the heart in order to make health care decisions affecting the heart failure patient's treatment. In many cases, the measurement of core body temperature and other patient data will enable the care provider to alter the patient's treatment to address the patient's condition (i.e., make the patient's condition less pathological). This treatment alteration may be as simple as alerting the patient to cease vigorous exercise, or as complex as modifying the operational parameters of the patient's pacing device (i.e., pacemaker).

Figure 4:
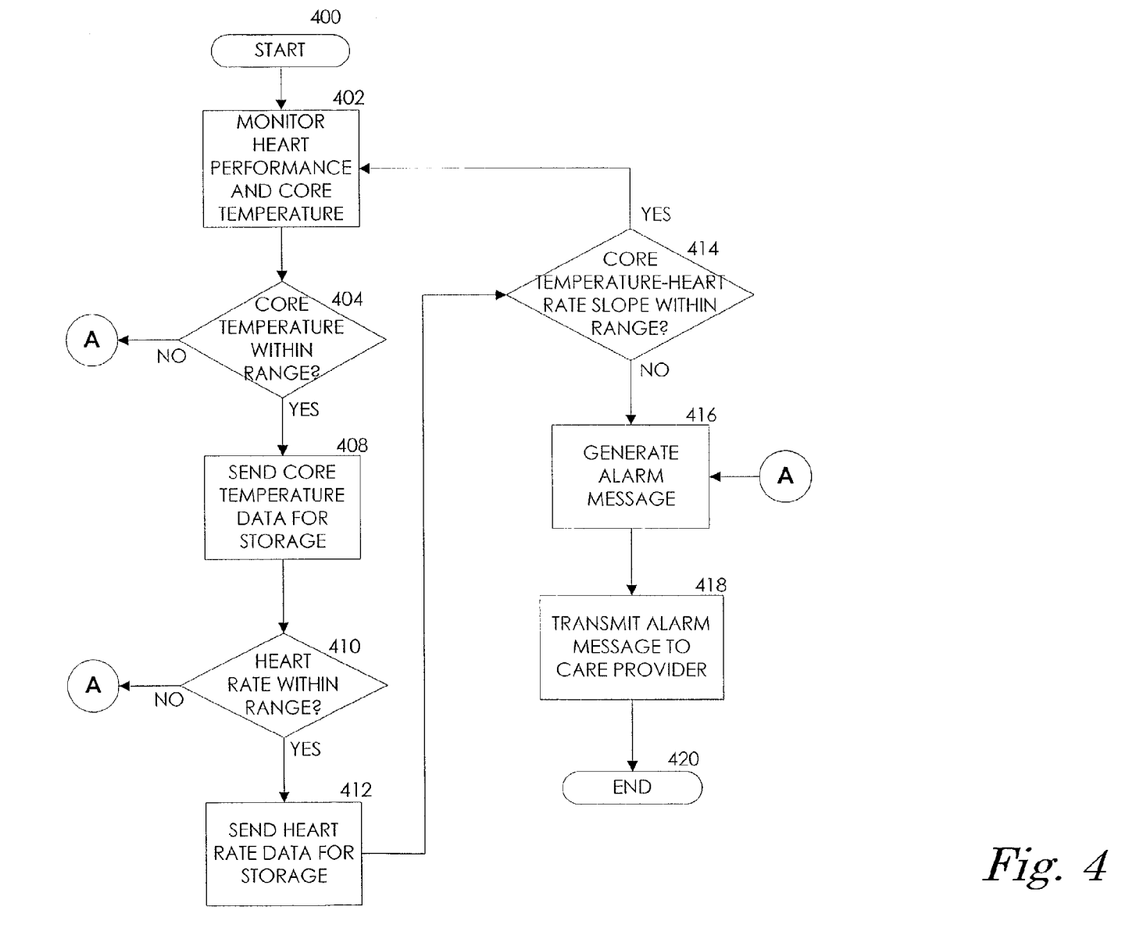
FIG. 4 is a flow chart depicting an exemplary method for monitoring and reporting core body temperature and heart rate levels for a heart failure patient.

FIG. 4 is a flow chart depicting an exemplary method for monitoring and reporting core body temperature and heart rate levels for a heart failure patient. The method of FIG. 4 begins at start block 400 and proceeds to step 402. At step 402, the heart performance and core body temperature of a heart failure patient is monitored. As described in connection with FIG. 2, the step of monitoring heart performance may be performed by an implanted heart monitor with a heart rate sensor operative to detect a heart rate. The core body temperature monitoring may be performed by and implanted heart monitor that uses a core body temperature sensor to determine the temperature of a venous blood pool.

The method proceeds from step 402 to decision block 404. At decision block 404, a determination is made as to whether the core body temperature is within a predetermined range. If the core body temperature is within the predetermined range, the method branches to step 408. On the other hand, if the monitored core body temperature is not within the predetermined range, the method branches to step 416 through connector A. In the exemplary method of FIG. 4, the predetermined range for core body temperatures may represent a range of core body temperature determined by a care provider to be a safe range for the patient. Those skilled in the art will appreciate that the range may differ from one heart failure patient to another and could, therefore, be configurable on a per-patient basis.

At step 416, an alarm message is generated to indicate that the measured core body temperature is outside of an acceptable range. The method proceeds from step 416 to step 418, wherein the alarm message is transmitted to the care provider. Those skilled in the art will appreciate that a single alarm may be used for any out-of-range condition. Alternatively, a separate alarm may be used for each out of range condition. The alarm message may include an indication of the measured data that has been determined to be out of the acceptable range. The method proceeds from step 418 to step 420 and heart performance and core body temperature monitoring is continued.

Returning now to decision block 404, if a determination is made that the core body temperature is within the predefined range, the method branches from decision block 404 to step 408. At step 408, the core body temperature data is transmitted for storage. In the remote heart monitoring system 300 of FIG. 3, the core body temperature data may be stored in the external monitor 312 for later transmission or may be stored in the monitoring station 318 in a centralized patient database. The method proceeds from step 408 to decision block 410.

At decision block 410, a determination is made as to whether the heart failure patient's heart rate is within a predefined acceptable range. If the patient's heart rate is outside of the acceptable range, the method branches to step 416, via connector A. The method proceeds from step 416 to generate an alarm indicating the out-of-range condition, as described above. If, at decision block 410, a determination is made that the heart rate is within the predefined acceptable range, the method branches from decision block 410 to step 412.

At step 412, the heart rate data is sent for storage. As described above, the heart rate data may be stored in an external monitor, a monitoring station, or any other acceptable storage means for subsequent retrieval. A method proceeds from step 412 to decision block 414. At decision block 414, a determination is made as to whether the core body temperature versus heart rate slope is within a predefined acceptable range. As described above in connection with FIG. 1, the relationship between the core body temperature and the heart rate (or any other indication of bodily activity) is a useful measurement for diagnosing a heart failure patient. If the slope is outside of the acceptable range, the method branches to step 416 and an alarm is generated as described above. If, on the other hand, the slope is within the range, the method branches from decision block 414 to step 402 and core body temperature monitoring is continued.

Although the present invention has been described in connection with various exemplary embodiments, those of ordinary skill in the art will understand that many modifications can be made thereto within the scope of the claims that follow. Accordingly, it is not intended that the scope of the invention in any way be limited by the above description, but instead be determined entirely by reference to the claims that follow.

What is claimed is:

1. A heart monitoring system, comprising:
    a temperature sensor for determining a core body temperature of a patient;
    a bodily activity sensor for determining a bodily activity level of the patient; and
    a heart monitor operatively connected to the temperature sensor and bodily activity sensor and configured to receive data representative of the core body temperature and the bodily activity level;
    the heart monitor further being configured to generate an alarm message upon determination that a relationship between the core body temperature and the bodily activity level is outside of a predefined range.

2. The heart monitoring system of claim 1, wherein the temperature sensor is of a configuration that allows the temperature sensor to be implanted in the patient's body.

3. The heart monitoring system of claim 1, wherein the bodily activity sensor is of a configuration that allows the bodily activity sensor to be implanted in the patient's body.

4. The heart monitoring system of claim 1, wherein the heart monitor is of a configuration that allows the external monitor to be implanted in the patient's body.

5. The heart monitoring system of claim 1, wherein the heart monitor is of a configuration that allows the heart monitor to be outside the patient's body and wherein the heart monitoring system includes a wireless communication link that allows wireless communications between the temperature sensor, bodily activity sensor and heart monitor.

6. The heart monitoring system of claim 1, wherein the heart is operative to determine a relationship between the core body temperature and the bodily activity level.

7. The heart monitoring system of claim 6, wherein the heart monitor is further operative to determine the slope of a two-dimensional representation of the relationship between the core body temperature and the bodily activity level.

8. The heart monitoring system of claim 6, wherein the heart monitor is further operative to generate an alarm when the relationship between the core body temperature and the bodily activity level is outside of a predetermined acceptable range.

9. The heart monitoring system of claim 6, wherein the heart monitor is further operative to transmit an alarm to a remote monitoring station, when the relationship between the core body temperature and the bodily activity level is outside of a predetermined acceptable range.

10. The heart monitoring system of claim 1, wherein the heart monitor is further operative transmit the core body temperature and the bodily activity level to a remote monitoring station.

11. A method for diagnosing a performance level of a heart in a patient, comprising the steps of:
    determining a core body temperature;
    determining a bodily activity level;
    determining a relationship between the core body temperature and the bodily activity level; and
    generating a first alarm message, in response to determining that the relationship between the core body temperature and the bodily activity level is outside of a predetermined acceptable relationship range.

12. The method of claim 11, further comprising the steps of:
    determining whether the core body temperature is within a predetermined acceptable temperature range; and
    generating a second alarm message, in response to determining that the core body temperature is outside of a predetermined acceptable temperature range.

13. The method of claim 12, further comprising the step of altering a patient treatment regimen, in response to determining that the core body temperature is outside of a predetermined acceptable temperature range.

14. The method of claim 11, further comprising the steps of:
    determining whether the bodily activity level is within a predetermined acceptable activity level range; and
    generating a third alarm message, in response to determining that the core body temperature is outside of a predetermined acceptable activity level range.

15. The method of claim 14, further comprising the step of altering a patient treatment regimen, in response to determining that the core body temperature is outside of a predetermined acceptable activity level range.

16. The method of claim 11, wherein the step of determining the bodily activity level comprises determining a patient blood pH level.

17. The method of claim 11, wherein the step of determining the bodily activity level comprises determining a patient ventilation rate.

18. The method of claim 11, wherein the step of determining the bodily activity level comprises determining a patient acceleration level.

19. The method of claim 11, further comprising the step of altering a patient treatment regimen, in response to a determination that the relationship between the core body temperature and the bodily activity level is outside of the predetermined acceptable relationship range.

20. An implantable heart monitor, comprising:
    a core body temperature sensor for determining a core body temperature of a patient;
    a bodily activity sensor for determining a bodily activity level of a patient;
    a transmission unit for transmitting the core body temperature and the bodily activity level to an external monitor; and
    a processing unit for calculating a relationship between the core body temperature and the bodily activity level and for generating an alarm message in response to a determination that the relationship is outside of a predefined acceptable range;
    wherein the transmission unit is further operative to transmit the alarm message to the external monitor.

21. The implantable heart monitor of claim 20, further comprising a pacing unit for pacing one or more of the patient's heart chambers.

22. The implantable heart monitor of claim 20, wherein the core body temperature sensor determines the core body temperature by sensing a myocardial muscle temperature and by correlating the myocardial muscle temperature to the core body temperature.

23. The implantable heart monitor of claim 20, wherein the core body temperature sensor determines the core body temperature by sensing a skeletal muscle temperature and by correlating the skeletal muscle temperature to the core body temperature.

24. The implantable heart monitor of claim 20, wherein the core body temperature sensor determines the core body temperature by sensing a skin temperature and by correlating the skin temperature to the core body temperature.

25. The implantable heart monitor of claim 20, wherein the core body temperature sensor determines the core body temperature by sensing a blood pH level and by correlating the blood pH level to the core body temperature.

26. The implantable heart monitor of claim 20, wherein the bodily activity sensor determines the bodily activity level by sensing a blood pH level and by correlating the blood pH level to the bodily activity level.

27. The implantable heart monitor of claim 20, wherein the bodily activity sensor determines the bodily activity level by sensing a blood $CO_2$ level and by correlating the blood $CO_2$ level to the bodily activity level.

28. The implantable heart monitor of claim 20, wherein the bodily activity sensor determines the bodily activity level by sensing a patient ventilation rate and by correlating the patient ventilation rate to the bodily activity level.

29. The implantable heart monitor of claim 20, wherein the bodily activity sensor determines the bodily activity level by sensing an oxygen consumption level and by correlating the oxygen consumption level to the bodily activity level.

30. A heart monitoring system, comprising:
    an implanted heart monitor having:
        a temperature sensor for determining a core body temperature of a patient;
        a bodily activity sensor for determining a bodily activity level of the patient; and
        a communication link for transmitting the core body temperature and the bodily activity level to an external monitor; and
    the external monitor operative to transmit the core body temperature and the bodily activity level to a care provider;
    wherein the implanted heart monitor is operative to send an alarm message to the external monitor in response to a determination that a relationship between the core body temperature and the bodily activity level is outside of a predefined acceptable range.

31. An implantable heart monitor, comprising:
    a core temperature level means for determining a core body temperature of a patient;
    an activity level means for determining a bodily activity level of a patient;
    a transmission means for transmitting the core body temperature and the bodily activity level to an external monitor; and
    a processing means for calculating a relationship between the core body temperature and the bodily activity level and for generating an alarm message in response to a determination that the relationship is outside of a predefined acceptable range;
    wherein the transmission means is further operative to transmit the alarm message to the external monitor.

* * * * *